United States Patent
Flemma, Jr. et al.

(10) Patent No.: US 7,562,711 B2
(45) Date of Patent: Jul. 21, 2009

(54) HYDRAULIC INJECTION OF BIOCIDE INTO TANKS

(75) Inventors: Edward Flemma, Jr., Farmington, NM (US); Mitch Mitchum, Farmington, NM (US)

(73) Assignee: Halliburton Energy Services, Inc., Duncan, OK (US)

( * ) Notice: Subject to any disclaimer, the term of this patent is extended or adjusted under 35 U.S.C. 154(b) by 310 days.

(21) Appl. No.: 11/620,982

(22) Filed: Jan. 8, 2007

(65) Prior Publication Data

US 2008/0164219 A1 Jul. 10, 2008

(51) Int. Cl.
*E21B 43/25* (2006.01)
*E21B 43/26* (2006.01)

(52) U.S. Cl. ............ 166/308.2; 166/75.11; 166/90.1; 166/91.1; 166/308.1; 210/747; 210/764; 405/129.1; 507/904

(58) Field of Classification Search ............ None
See application file for complete search history.

(56) References Cited

U.S. PATENT DOCUMENTS

| | | | |
|---|---|---|---|
| 4,552,591 A * | 11/1985 | Millar ............ | 106/18.33 |
| 4,647,589 A | 3/1987 | Valone | |
| 5,421,412 A | 6/1995 | Kelly et al. | |
| 6,500,345 B2 * | 12/2002 | Constantine et al. ........ | 210/747 |
| 7,374,692 B2 * | 5/2008 | Hesse et al. ............ | 210/748 |
| 2004/0120853 A1 * | 6/2004 | Carpenter et al. ........ | 422/37 |
| 2005/0016933 A1 * | 1/2005 | Perlich et al. ........ | 210/754 |
| 2008/0115930 A1 * | 5/2008 | Peters et al. ............ | 166/248 |
| 2008/0127662 A1 * | 6/2008 | Stanfield et al. ........ | 62/175 |
| 2008/0142224 A1 * | 6/2008 | Wilson ............ | 166/308.2 |
| 2008/0169098 A1 * | 7/2008 | Christopher et al. ........ | 166/275 |

OTHER PUBLICATIONS

"Stimulation and Fluids Data—Bactericides/Biocides," Halliburton Coiled Tubing Handbook; Sep. 2005; pp. 3-44 to 3-46.

* cited by examiner

*Primary Examiner*—George Suchfield
(74) *Attorney, Agent, or Firm*—John W. Wustenberg; Conley Rose, P.C.

(57) ABSTRACT

A method of servicing a wellbore comprising transporting at least two portable tanks to a well site to be serviced, and hydraulically injecting biocide into a first of the two tanks, wherein a second of the two tanks serves as a fluid source for conveying the biocide into the first tank.

23 Claims, 1 Drawing Sheet

HYDRAULIC INJECTION OF BIOCIDE INTO TANKS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

This disclosure relates to the field of oilwell stimulation, drilling, and recovery. In particular, the present disclosure relates to an apparatus and method for injecting biocide into a tank to treat oilfield water or oilfield fluid. More particularly, the present disclosure is directed to an apparatus and a method for injecting biocide at a position near the bottom of a tank. Also disclosed is a method of efficiently treating a plurality of tanks with biocide.

2. Background of the Invention

As is well-known to those skilled in the art, the presence of microbiological contaminants in liquid systems causes problems typified by increased corrosion rates and plugging of conduits, filters, pumps, etc. During petroleum production, it is often desirable to inhibit microbiological growth in substrates which include aqueous or aqueous-hydrocarbon liquids found in subterranean well holes, in surface ponds or reservoirs of crude oil, in salt water separated from crude oils, and on the various metal equipment which comes into contact with these fluids. Such equipment includes tanks, pumps, structural members, etc.

Natural and synthetic polymers are used in the oil industry in methods of well stimulation, drilling, and recovery. These polymers are used, for example, in water flood, fracturing and drilling fluids, and are exposed to an environment that is conducive to the growth of microorganisms. Some of the most favorable environments for bacteria are dirty frac tanks and mixing water. Microorganisms, for example bacteria, feed on polymers (for example, gel stabilizers used in aqueous fracturing fluid processes) by releasing enzymes. The enzymes degrade the polymer to sugar, and the microorganisms absorb the sugar through their cell walls. When conditions are favorable, some species may attain maximum concentrations within twenty-four hours and may be the chief cause of polymer degradation. The growth of microorganisms on the polymers used in these fluids can thus materially alter the physical characteristics of the fluids. For example, bacterial action can deteriorate the polymer, leading to a loss of viscosity and rendering the fluids ineffective for the intended purpose. Fluid degradation may also lead to the formation of a large biomass, which may plug the formation and reduce permeability.

A wide variety of biocides have been used in various environments, for example bactericides are used to control sulfate-reducing bacteria, slime-forming bacteria, iron-oxidizing bacteria and bacteria that attack polymers in fracture and secondary recovery fluids. Biocides should be handled with caution, to prevent personal and environmental contamination. Biocides are, by their very nature, dangerous to handlers. Handlers must avoid eye and skin contact and, when liquid biocides are utilized, must avoid splashing or spilling the liquid biocide, as spilled biocides can contaminate potable water sources.

Often, tanks are treated with biocide to inhibit microbiological growth. Commonly, biocide is introduced into the tank to be treated by being dropped into the top of the tank. This treatment routinely involves a handler climbing to the top of the tank (or truck), which may be 12 feet to 16 feet high, in order to 'drop' the biocide into the tanks. This climbing inherently creates a danger of falling, especially in inclement weather and when there are no latches available for the use of a safety harness. Attachments to ladders and to the tops of tanks that would be necessary to enable a safety harness to be latched are easily damaged during loading/unloading of the tanks, and make positioning the tanks on location very difficult. The footpad available for placing multiple tanks often mandates placing the tanks in close proximity. This negates the practicality of such attachments for latching a safety harness. Furthermore, cranes, hoists, etc., are not normally available on location during these operations and are not economically viable to use as a safe work platform. When tanks are located in close proximity to each other, it is not uncommon for the handler dropping the biocide to climb to the top of an outer tank and hop from tank to tank in order to introduce the biocide into the desired tank. This unsafe practice becomes even more dangerous when the tank to be treated is difficult to get to and when weather conditions, such as snow, wind and rain, exacerbate the difficulty of reaching the treatment tank.

Accordingly, an ongoing need exists for an apparatus and a method for treating a tank with biocide that minimizes the possibility of contamination of the environment and eliminates the risk of injury to or death of a handler from falling a distance during treatment of the tank.

BRIEF SUMMARY OF SOME OF THE PREFERRED EMBODIMENTS

Disclosed herein is a method of servicing a wellbore comprising transporting at least two portable tanks to a well site to be serviced; and hydraulically injecting biocide into a first of the two tanks, wherein a second of the two tanks serves as a fluid source for conveying the biocide into the first tank.

Further disclosed herein is an apparatus for hydraulically injecting biocide into a treatment tank comprising an inlet hose, a pump, an outlet hose, and a means for introducing biocide into the system, wherein the inlet hose is connected to the pump, and the pump is further connected to the outlet hose, and the outlet hose is connectable to the means for introducing biocide into the apparatus which contains a biocide to treat the treatment tank. The means for introducing biocide into the system may comprise an inverted tee pipe attached with a first isolation valve to a biocide inlet pipe and optional hopper through which biocide enters the means for introducing biocide into the system, wherein the tee pipe is further attached to a second isolation valve between the pump and the tee pipe. The hopper may be a funnel and need not be permanently attached to the biocide inlet pipe. The apparatus, e.g., the inlet hose, the pump, the outlet hose, and the means for introducing biocide into the system, may be portable.

Further disclosed herein is a method for hydraulically injecting biocide into an oilfield fluid with the apparatus described herein, the method comprising connecting the inlet hose to a feed tank of feed fluid via a feed tank discharge valve; connecting the tee pipe to the treatment tank containing the oilfield fluid via a treatment tank discharge valve; connecting the means for introducing biocide into the system to the outlet hose; opening the first isolation valve; introducing an amount of biocide into the biocide inlet pipe optionally via the hopper; closing the first isolation valve; opening the feed tank discharge valve, whereby the pump is primed; opening the second isolation valve, whereby feed fluid mixes with the biocide; turning on the pump to pressurize the tee pipe and the outlet hose; and opening the treatment tank discharge valve, whereby the biocide is injected into the treatment tank. The method may further comprise closing the feed tank discharge valve and the treatment tank discharge valve and disconnecting the system from the tanks. The oilfield fluid may be mix water; the feed fluid may be water; the oilfield fluid may be a fracturing fluid; the oilfield fluid may be a drilling fluid; or combinations thereof. In an embodiment, the oilfield fluid is mix water, and the method further comprises, after injecting biocide into the tank, using the mix water in a fracturing fluid. The method may further comprise selecting an effective microbial inhibiting amount of biocide. Where the oilfield fluid to be treated is not in the treatment tank upon injection of the biocide, the method may further comprise adding the oilfield fluid to the treatment tank containing biocide to treat the oilfield fluid with biocide. The treatment tank discharge valve may be located within the lower half of the treatment tank such that the biocide is injected into the lower half of the treatment tank. Operation of at least one of the valves may be automated.

Further disclosed herein is a method for efficiently treating a plurality of tanks with biocide, the method comprising rigging up an apparatus as disclosed herein to treat a first treatment tank with biocide; rigging up a second apparatus as disclosed herein to a second treatment tank during injection of biocide into the first treatment tank; rigging down the first apparatus upon completion of injection of biocide into the first treatment tank and during injection of the second treatment tank, and rigging the first apparatus up to an optional third treatment tank to be treated during injection of the second treatment tank. The method may further comprise continuing to "leap frog" in this manner until the plurality of tanks has been treated with biocide. The first treatment tank may comprise mix water.

Further disclosed herein is an apparatus for hydraulically injecting biocide into a treatment tank, the apparatus comprising a means for connecting to a feed tank discharge valve, a suction hose, a pump having an inlet and an outlet, a discharge hose, a biocide launcher having a biocide inlet and a fluid pathway comprising a fluid inlet and a fluid outlet, and a means for connecting to a treatment tank discharge valve; wherein the means for connecting to a feed tank discharge valve is connected to the suction hose, wherein the suction hose is connected to the pump inlet, wherein the pump outlet is attached to the discharge hose, wherein the discharge hose is connected to the biocide launcher fluid inlet, wherein the biocide launcher fluid outlet is attached to the means for connecting to a treatment tank discharge valve, wherein the biocide launcher fluid inlet comprises an isolation valve, and wherein the biocide launcher biocide inlet is located between the biocide launcher fluid inlet isolation valve and the biocide launcher fluid outlet. The overall system my further comprise a feed tank of oilfield water and a treatment tank of oilfield mix water.

The foregoing has outlined rather broadly the features and technical advantages of the present disclosure in order that the detailed description that follows may be better understood. Additional features and advantages of the apparatus and method will be described hereinafter that form the subject of the claims of this disclosure. It should be appreciated by those skilled in the art that the conception and the specific embodiments disclosed may be readily utilized as a basis for modifying or designing other structures for carrying out the same purposes of the present disclosure. It should also be realized by those skilled in the art that such equivalent constructions do not depart from the spirit and scope of the apparatus and method as set forth in the appended claims.

BRIEF DESCRIPTION OF THE DRAWINGS

For a detailed description of the preferred embodiments of the apparatus and methods of the present disclosure, reference will now be made to the accompanying drawing in which.

DETAILED DESCRIPTION OF THE PREFERRED EMBODIMENTS

Figure 1:
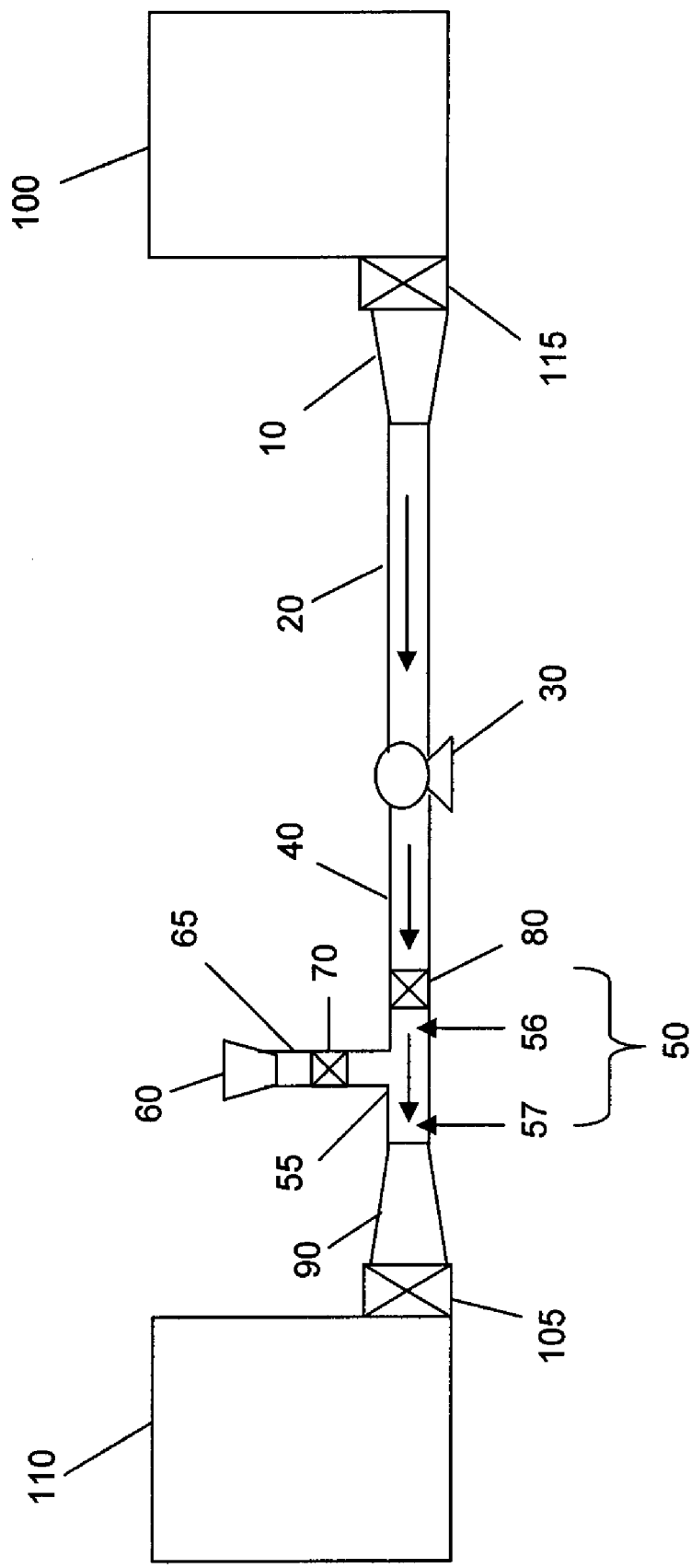
FIG. 1 is a schematic of an embodiment of an apparatus according to the present disclosure.

As used herein, the terms "oil field fluids" or "wellbore servicing fluid" are meant to include those fluids having oil field applications, for example fluids suitable for pumping down hole to service or treat a wellbore. As used herein, a "servicing fluid" refers to a fluid used to drill, complete, work over, fracture, repair, or in any way prepare a wellbore for the recovery of materials residing in a subterranean formation penetrated by the wellbore. It is to be understood that "subterranean formation" encompasses both areas below exposed earth and areas below earth covered by water such as ocean or fresh water. Examples of servicing fluids include, but are not limited to cement slurries, drilling fluids or muds, spacer fluids, fracturing fluids or completion fluids, all of which are well known in the art. Without limitation, servicing the wellbore includes positioning the servicing fluid in the wellbore to isolate the subterranean formation from a portion of the wellbore; to support a conduit in the wellbore; to plug a void or crack in the conduit; to plug a void or crack in a cement sheath disposed in an annulus of the wellbore; to plug an opening between the cement sheath and the conduit; to prevent the loss of aqueous or non-aqueous drilling fluids into loss circulation zones such as a void, vugular zone, or fracture; to be used as a fluid in front of cement slurry in cementing operations; to seal an annulus between the wellbore and an expandable pipe or pipe string; to fracture a formation; or combinations thereof. In some embodiments, oil field fluids may have increased viscosity via addition of viscosifying agents such as polymers, whether polysaccharide or synthetics.

The term "oil field waters" as used herein includes waters used in secondary recovery, water used to hydrate polymers and water used in tertiary or enhanced oil recovery methods. The oil filed waters may be fresh water or salt water, e.g., an unsaturated aqueous salt solution or a saturated aqueous salt solution such as brine or seawater. In various embodiments, one or more biocides may be added to one or more oil field fluids and/or wellbore servicing fluids. The term "biocide" includes any compound or agent used to kill biological organisms and/or microorganisms, including antibiotics, bacterialcides, fungicides, pesticides, herbicides, insecticides, miticides, rodenticides, or combinations thereof. As used herein, the term "swedge" is meant to refer to any connection that serves to change the size or line threads with another connection.

Disclosed herein are an apparatus and methods for treating tanks with biocide. In embodiments, the apparatus and methods eliminate the need for climbing to the top of a treatment tank to inject biocide into the tank. In embodiments, biocide is injected into the bottom portion of a tank. In an embodiment, the biocide is injected within 0 to 6 feet of the ground, alternatively, at a point below the midpoint of the tank. In embodiments, the apparatus of the present disclosure comprises components that are portable. In embodiments, the components are easily handled by one person and can be carried in, for example, a pickup truck.

The apparatus is fluidly connected from a suction tank for holding a fluid, commonly water, which is used to carry biocide from a biocide launcher to a treatment tank, i.e., a tank containing the fluid that is to be treated with biocide. The fluid to be treated with biocide may be an oil field fluid, oil field waters, and/or a wellbore servicing fluid. In an embodiment, biocide may be incorporated into oil field water or oil field polymeric fluid by injecting the biocide into the water used for making the polymer solution, a concentrated polymer solution, and/or a dilute polymer solution. In an embodiment the fluid to be treated is oil field water and/or oil field fluid polymers, e.g., polyacrylamides and polysaccharides, guar gum, hydroxypropyl guar gum, starches, and hydroxymethycellulose polymers used in fracturing fluids for oil well stimulation. In alternative embodiments, the fluid to be treated may be an aqueous slurry and/or oil field water to be used to produce an aqueous slurry, for example an aqueous drilling fluid, fracturing fluid, spacer fluid, displacement fluid, completion fluid, cement, etc.

In embodiments, the biocide effectively controls the growth of various microorganisms. In embodiments, the biocide is a bactericide affective against sulfate-reducing bacteria, slime-forming bacteria, iron-oxidizing bacteria and/or bacteria that attack polymers in fracture and secondary recovery fluids. In embodiments, the biocide is effective against fungi and algae.

In embodiments, the biocide is a liquid, for example a liquid concentrate. In embodiments, the bactericide is caustic, which is used to adjust the treating water pH upward. Caustic may be added such that the pH of the treated tank is greater than 11 so that bacteria are effectively eliminated. The liquid biocide BE-3, available from Halliburton Energy Services, is an effective, fast-killing biocide at low concentrations (0.1 gal/Mgal) and is useful for fluid at pH less than about 7. The liquid biocide, CAT-1, available from Halliburton Energy Services is effective for controlling certain sporulated forms of bacteria that are may be resistant to other biocides.

Alternatively, the biocide is a solid, such as a powder. Suitable solid biocides include the rapid-killing, broad-spectrum biocide BE-3S, the broad spectrum biocide BE-5 which is effective against most types of bacteria, fungi, and algae, and the broad-spectrum bactericide BE-6. These biocides are available from Halliburton Energy Services.

Discussion of the apparatus and the operation of the apparatus for hydraulic injection of a biocide into one or more tanks to be used in a wellbore service will now be made with reference to FIG. 1. Two tanks, suction tank 100 and treatment tank 110 are placed in fluid communication via suction hose 20, pump 30, discharge hose 40, and biocide launcher 50. Tanks 100 and 110 include any portable tank that may be moved to and from a well site and used to prepare a wellbore servicing fluid or otherwise prepare the site for a wellbore service. Typically such tanks may be open top or open air tanks that are placed on the ground. However, such tanks may also be enclosed tanks, for example tanker trailers or tanker trucks. In an embodiment, suction tank 100 is a portable water hauler, for example a trailer mounted water tank or over-road tanker truck. In an embodiment, tanks 100 and 110 are frap tanks used during a wellbore fracturing operation. Such frac tanks may include water, additives, polymers, slurries, solutions, prepared fracturing fluids, recovered fracturing fluids, waste fracturing fluid, other waste fluids, recovered wellbore fluids, etc. In embodiments, suction tank 100 comprises any container holding fluid, for example tank 100 may comprise a fluid-filled container mounted to a pick-up truck or buckets that can be refilled with fluid as needed.

Suction tank 100, a feed tank, comprises suction tank discharge valve 115. Suction tank discharge valve 115 is swedged via suction tank swedge 10 to suction hose 20. Suction hose 20 is further connected to the inlet of pump 30. Outlet from pump 30 is fluidly connected to discharge hose 40. Discharge hose 40 is further connected to biocide launcher 50, which in turn is attached to treatment tank swedge 90, which in turn is attached to treatment tank 110 via treatment tank discharge valve 105. Optionally, a length of hose or conduit may be included between treatment tank swedge 90 and biocide launcher 50.

In an embodiment, biocide launcher 50 further comprises biocide launcher fluid inlet isolation valve 80, biocide launcher biocide inlet isolation valve 70 and optional hopper 60. In embodiments, the biocide launcher comprises a biocide inlet in fluid communication with a fluid pathway. In an embodiment, the biocide inlet comprises hopper 60, biocide inlet pipe 65 and biocide launcher biocide inlet isolation valve 70. In embodiments, hopper 60 is connected to biocide inlet pipe 65 and biocide inlet pipe 65 is further connected to biocide launcher biocide inlet isolation valve 70. In embodiments, the biocide launcher fluid pathway has a fluid inlet 56 and a fluid outlet 57. In embodiments, the biocide launcher fluid pathway is provided by an inverted "T" pipe section 55, fluid inlet 56 of the T pipe being further connected to biocide launcher fluid inlet isolation valve 80, and fluid outlet 57 of the T pipe being further connected to treatment tank swedge 90.

In an embodiment, suction tank swedge 10 is a 4" swedge to a ¾" female CamLoc connection, suction hose 20 and discharge hose 40 are ¾" hoses, pump 30 is a ¾" pump, and treatment tank swedge 90 is a 4" swedge to a 4" male CamLoc connection. In an embodiment, biocide launcher 50 comprises a 4" pipe 55 that is swedged at biocide launcher fluid inlet 56 to a 1" biocide launcher fluid inlet isolation valve 80 and further to a ¾" female CamLoc discharge connection for attachment to ¾" discharge hose 40. Biocide launcher fluid outlet 57 is swedged with a 4" female CamLoc discharge connection to treatment tank discharge valve 105 via 4" treatment tank swedge 90 to 4" male CamLoc connection. In this embodiment, T pipe section 55 is swedged and fluidly connected to 2" biocide launcher biocide inlet isolation valve 70. Optional hopper 60 may be a collection device, such as a funnel, and may be attached to, not attached to, or removably attached to biocide inlet pipe 65, which in an embodiment may be a 2" pipe to match 2" biocide launcher biocide inlet isolation valve 70. Pump 30 may be any pump known to one of skill in the art, for example, an electric pump, and may run off, for example, a pickup truck alternator and AC converter, or other means of power such as a battery or portable generator. In embodiments, one or more valves of the apparatus are automated as known to those of skill in the art. In embodiments, one or more of the valves are manually operated.

In an embodiment, the method disclosed herein comprises rigging up, by any means known to one of skill in the art, the apparatus described above between a suction tank 100 which is the tank for the fluid to be used as a fluid source (e.g., water) and a treatment tank 110 which is the tank to be treated. By way of example, and without limiting to this embodiment, the method comprises: rigging the suction tank swedge 10 to the suction tank 100 via suction tank discharge valve 115; connecting suction hose 20 to the inlet of pump 30 and to suction tank swedge 10; connecting biocide launcher 50 to treatment tank 110 via treatment tank discharge valve 105 and treatment tank swedge 90; connecting discharge hose 40 from the outlet of pump 30 to the biocide launcher fluid inlet 56 side of the biocide launcher; assuring that all valves are closed; opening the biocide launcher biocide inlet isolation valve 70 and placing an effective antibacterial amount of biocide to treat the fluid to be treated into biocide inlet pipe 65 optionally via hopper 60; closing the biocide launcher biocide inlet isolation valve 70; opening suction tank discharge valve 115 and allowing suction tank fluid to flood and prime pump 30; opening biocide launcher fluid inlet isolation valve 80 allowing fluid to flood the fluid pathway of the biocide launcher and mix with the biocide; turning on pump 30 to pressurize discharge hose 40 and "T" pipe section 55; opening treatment tank discharge valve 105 whereby fluid and biocide are injected into the bottom of treatment tank 110. Upon injection of biocide into treatment tank 110, pump 30 is turned off, suction tank discharge valve 115 and treatment tank discharge valve 105 are closed and the apparatus may be removed from fluid connection with the tanks.

The amount of biocide in the biocide launcher will depend on a number of factors including: the particular biocide being used, its effectiveness at various activity levels, the particular oil field water or oil field servicing fluid to be treated, the conditions of use of the water or polymer and the extent of prior contamination by bacteria, the time period of growth inhibition desired, the general environment, and etc. It is thus not possible to quantitatively delineate a minimum effective bacterial inhibiting amount. Large excesses may be undesirable from an economic standpoint. Determining an effective antibacterial amount is understood by those of skill in the art.

Often, tanks, e.g. frac tanks, contain several gallons of bacteria-ridden decomposed gel from previous jobs. In embodiments of the present disclosure, biocide is injected into treatment tank 110 prior to the addition of fluid to be treated into the treatment tank in order to place a high enough concentration of biocide in the bottom of the tank where bacteria and a large portion of their enzymes can be destroyed. For example, tank 110 may be pre-treated with an amount of biocide and subsequently partially or completely filled with a wellbore servicing fluid or oil field waters, and may be subsequently treated one or more additional times with biocide during or following filling of the tank. For example, the tank 110 may be treated with biocide one or more times before, during, or after filling and/or refilling. In embodiments, biocide is injected into a treatment tank that is partially filled with a fluid to be treated.

In an embodiment, two or more of the disclosed apparatus are employed in order to facilitate the treatment of a plurality of tanks with biocide. In this embodiment, a first apparatus is rigged up as described hereinabove. Once pumping of biocide into a first treatment tank has commenced, rigging up of a second apparatus is carried out to treat a second treatment tank with biocide. Once pumping of biocide into the second treatment tank commences and upon completion of injection of biocide into the first treatment tank, the first apparatus is rigged down and, if more tanks require biocide treatment, is rigged up to a third treatment tank during injection of biocide into the second tank. This process continues with rigging down and rerigging to subsequent tanks commencing during injection of biocide into a previous tank. By utilizing more than one apparatus of the present disclosure, a plurality of tanks can be treated with biocide in less time than if a single apparatus is used for the injection of all of the tanks, i.e. the use of more than one apparatus allows for a parallel operation, rather than operation in series. The use of more than one apparatus of the present disclosure may prove economical as 20-30 tanks are often on location and, frequently, many of these tanks require antimicrobial treatments. In further embodiments, when a plurality of tanks to be treated are in close enough proximity, suction tank 100, suction tank discharge valve 115, suction tank swedge 10, suction hose 20, pump 30, and discharge hose 40 can be used to treat multiple treatment tanks 110 using multiple biocide launchers 50, treatment tank swedges 90, treatment tanks 110 and treatment tank discharge valves 105.

The apparatus and method disclosed herein may be used in conjunction with preparing for, conducting, or follow-up to any wellbore servicing method requires tanks for storage of materials that may be subject to microbial growth. In various embodiments, one or more fluids stored in a tank and treated with biocide as described herein is pumped down hole and used to service a wellbore. In other embodiments, the method and apparatus disclosed herein is used to treat one or more fluids recovered from a wellbore during service of the wellbore and subsequently stored in a tank. In other embodiments, a tank may be delivered to a well site, optionally pretreated. A fluid may be stored in the tank, treated one or more times, and pumped down hole. The fluid may be recovered and stored in the same or different tank, which may be optionally pretreated. The recovered fluid may optionally be treated one or more times, and optionally pumped down hole again or otherwise disposed of. Such sequences may be repeated.

In embodiments, the treatment of oilfield tanks with biocide using the method and apparatus of the present disclosure may involve charging a certain fee per tank of fluid treated with biocide.

While preferred embodiments of the apparatus and methods for utilizing the apparatus have been shown and described, modifications thereof can be made by one skilled in the art without departing from the spirit and teachings of the present disclosure. The embodiments described herein are exemplary only, and are not intended to be limiting. For example, while the fluids referred to in this disclosure are commonly encountered in the oilfield, the apparatus and method of the present disclosure are suitable for the injection of other materials into tanks as well. Many variations and modifications of the apparatus and methods disclosed herein are possible and are within the scope of this disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A method of servicing a wellbore comprising:
transporting at least two portable tanks to a well site to be serviced; and
hydraulically injecting biocide into a first of the two tanks, wherein a second of the two tanks serves as a fluid source for conveying the biocide into the first tank.

2. The method of claim 1 wherein hydraulically injecting further comprises placing a portable biocide injection apparatus in fluid communication between the two tanks.

3. The method of claim 2 further comprising disconnecting the portable biocide injection apparatus from the first tank, connecting the portable injection apparatus to a third tank, and hydraulically injecting biocide into the third tank.

4. The method of claim 1 wherein the portable biocide injection apparatus is located on or near the ground.

5. The method of claim 1 wherein the biocide is injected into the first tank prior to filing the first tank.

6. The method of claim 1 wherein the biocide is injected into the first tank during or after the tank is partially or completely filled.

7. The method of claim 1 wherein the biocide is injected more than once into the first tank.

8. The method of claim 1 further comprising placing the treated fluid from the first tank into the wellbore.

9. The method of claim 8 wherein the treated fluid is a fracturing fluid or a component thereof.

10. The method of claim 9 wherein the fracturing fluid comprises one or more polymers.

11. The method of claim 8 wherein the treated fluid is a drilling fluid, completion fluid, spacer fluid, cement slurry, or a component thereof.

12. The method of claim 8 further comprising recovering fluid from the wellbore, placing the recovered fluid into a recovery tank, and hydraulically injecting biocide into the recovery tank to produce a treated recovered fluid.

13. The method of claim 12 wherein the recovery tank is pretreated before placing the recovered fluid therein.

14. The method of claim 12 further comprising disposing of the treated recovered fluid.

15. The method of claim 12 further comprising placing the treated recovered fluid into the wellbore.

16. The method of claim 8 further comprising transporting the tanks from the well site upon completion of the wellbore service.

17. The method of claim 1 further comprising hydraulically injecting biocide into a third tank simultaneously with hydraulically injecting biocide into the first tank.

18. The method of claim 17 wherein the second tank serves as a fluid source for conveying the biocide into the third tank.

19. The method of claim 17 wherein a fourth tank serves as a fluid source for conveying the biocide into the third tank.

20. The method of claim 1 wherein the second tank is a water trailer or a water tanker truck.

21. The method of claim 1 further comprising recovering fluid from the wellbore, placing the recovered fluid into a recovery tank, and hydraulically injecting biocide into the recovery tank to produce a treated recovered fluid.

22. The method of claim 21 further comprising placing the treated recovered fluid into the wellbore.

23. The method of claim 21 wherein the treated fluid is a fracturing fluid or a component thereof.

* * * * *